US005239101A

United States Patent [19]
Bokerman et al.

[11] Patent Number: 5,239,101
[45] Date of Patent: Aug. 24, 1993

[54] ANHYDROUS PROCESS FOR PREPARATION OF POLYORGANOSILOXANES

[75] Inventors: Gary N. Bokerman, Midland, Mich.; David E. Puckett, Taylor Mill; Larry H. Wood, Campbellsburg, both of Ky.

[73] Assignee: Dow Corning Corporation, Midland, Mich.

[21] Appl. No.: 994,582

[22] Filed: Dec. 21, 1992

[51] Int. Cl.$^5$ ................................................. C07F 7/08
[52] U.S. Cl. ..................................... 556/451; 556/453; 556/456
[58] Field of Search .................. 556/451, 453, 456

[56] References Cited

U.S. PATENT DOCUMENTS

| | | | |
|---|---|---|---|
| 2,457,677 | 12/1948 | Hyde | 260/448 L |
| 2,467,976 | 4/1949 | Hyde | 260/448 L |
| 2,491,843 | 12/1944 | Wilcock | 260/448 L |
| 2,779,776 | 1/1957 | Hyde | 260/448 L |
| 4,310,680 | 1/1982 | Kötzsch et al. | 556/453 X |
| 4,609,751 | 9/1986 | Hajjar | 556/456 |
| 5,011,962 | 4/1991 | Staiger et al. | 556/453 |
| 5,075,479 | 12/1991 | Boherman et al. | 556/453 |
| 5,126,470 | 6/1992 | Schulz et al. | 556/453 |

Primary Examiner—Paul F. Shaver
Attorney, Agent, or Firm—William F. Boley

[57] ABSTRACT

The present invention is an anhydrous process for preparing organosiloxy end-blocked polyorganosiloxanes from chlorine end-terminated polyorganosiloxanes. The process comprises contacting an anhydrous mixture comprising a chlorine end-terminated polyorganosiloxane and an organodisiloxane with a rearrangement catalyst, where the rearrangement catalyst facilitates a chlorine and organosiloxy exchange between the chlorine end-terminated polyorganosiloxane and the organodisiloxane forming a organochlorosilane as a by-product. The organochlorosilane is continuously removed from the process providing a means by which the chlorine displaced from the chlorine end-terminated polyorganosiloxane can be effectively removed from the organosiloxy end-blocked polyorganosiloxanes in a useable form. The present process is especially useful for the rearrangement of chlorine end-terminated polyorganosiloxanes having one or more hydrogen atoms bonded to silicon to organosiloxy end-blocked polyorganohydrosiloxanes.

22 Claims, No Drawings

ANHYDROUS PROCESS FOR PREPARATION OF POLYORGANOSILOXANES

BACKGROUND OF INVENTION

The present invention is an anhydrous process for the rearrangement of chlorine end-terminated polyorganosiloxanes to form organosiloxy end-blocked polyorganosiloxanes. The process is especially useful for the rearrangement of chlorine end-terminated polyorganosiloxanes having one or more hydrogen atoms bonded to silicon. The process comprises contacting a mixture comprising a chlorine end-terminated polyorganosiloxane and an organodisiloxane with a rearrangement catalyst. The rearrangement catalyst is effective in facilitating a chlorine and organosiloxy exchange between the chlorine end-terminated polyorganosiloxane and the organodisiloxane and may further effect rearrangement of the silicon to oxygen bonds within the chlorine end-terminated polyorganosiloxane and the silicon to oxygen bonds within the organosiloxy end-blocked polyorganosiloxanes. In the present process, the organodisiloxane serves as a source of (1) an organosiloxy end-blocker which displaces the chlorines of the chlorine end-terminated polyorganosiloxanes and (2) an organosilyl component which binds with the displaced chlorine to form a volatile organochlorosilane. The volatile organochlorosilane is continuously removed from the process.

Since the early work of Hyde, U.S. Pat. No. 2,457,677, issued Dec. 28, 1948, it has been known that diorganodihalosilanes in the presence of water hydrolyze to form a mixture of cyclic diorganosiloxanes and short-chained linear diorganosiloxanes along with hydrogen chloride as a by-product. Hyde also observed in this patent that the presence of a triorganosilane in the process could result in polydiorganosiloxanes that were triorganosiloxy end-blocked.

Hyde, U.S. Pat. No. 2,467,976, issued Apr. 19, 1949, teaches that the viscosity of polydimethylsiloxanes produced by the hydrolysis of diorganodichlorosilanes could be increased by refluxing the polydimethylsiloxanes with hydrochloric acid effecting rearrangement of silicon to oxygen bonds within the polydimethylsiloxanes. In U.S. Pat. No. 2,779,776, Hyde further teaches that the acid concentration is important in determining the equilibrium viscosity of the polydimethylsiloxane products.

Wilcock, U.S. Pat. No. 2,491,843, issued Dec. 20, 1949, described processes, similar to those described by Hyde, for the production of polyorganohydrosiloxanes.

The hydrolysis of diorganodichlorosilanes to form a mixture of cyclic siloxanes and short-chain linear siloxanes with the liberation of chlorine continues to be an important first step in commercial processes for producing higher molecular weight polyorganosiloxanes. However, the chlorine displaced from the diorganodichlorosilanes during the hydrolysis process creates several problems. For example, it is known that residual chloride present in polyorganosiloxane fluids can reduce shelf-life of the fluids by effecting viscosity changes. Therefore, any process for producing higher molecular weight polyorganosiloxanes from a hydrolyzate must be capable of controlling the level of chlorine present in the polyorganosiloxanes. A second problem is disposition of the displaced chlorine after recovery from the process. Because of the economic value of chlorine and the cost of disposal of chlorine, it is preferred to recover the chlorine for use in the same or different processes. Several processes have been described to deal with these problems but each suffers from various shortcomings.

For example, in one process, the hydrolysis is run in the presence of a stoichiometric excess of water, resulting in the production of cyclosiloxanes, short-chained hydroxyl terminated polysiloxanes, and aqueous hydrogen chloride. The partitioning of the chlorine into the aqueous phase is an exothermic process requiring that the reactor be cooled to maintain a desired temperature. Furthermore recovery of the chlorine from the process in the form of anhydrous hydrogen chloride must typically be accomplished by an energy intensive distillation of a $HCl-H_2O$ azeotrope.

In another process, as exemplified by Hajjar, U.S. Pat. No. 4,609,751, issued Sep. 2, 1968, the process is run with about a stoichiometric equivalence of water with the consequential generation of anhydrous hydrogen chloride. The resultant product is cyclosiloxanes and chlorine end-terminated polyorganosiloxanes. Although this process provides a satisfactory solution to the recovery of displaced chlorine, to assure satisfactory low-levels of chlorine in the final polyorganosiloxane product a multi-step process is typically required. The chlorine-terminated polyorganosiloxanes are typically washed with one or more portions of water to form hydroxyl-terminated polyorganosiloxanes and a weak aqueous hydrogen chloride solution which can be returned to the process. These hydroxyl-terminated polyorganosiloxanes can then be further processed to produce long-chain polyorganosiloxanes. This additional wash step increases the cost of producing long-chain polyorganosiloxanes.

An additional problem associated with the described processes is that the process conditions can be sufficiently severe to cause reaction of desired silicon-bonded hydrogen when present in the polyorganosiloxanes. Therefore, these process are not entirely suitable for the production of polyorganohydrosiloxanes.

Therefore, an objective of the present invention is to provide a process for converting chlorine-end terminated polyorganosiloxanes to polyorganosiloxanes without first converting the end-terminal chlorine to end-terminal hydroxyl. A second objective is to provide a process for making polyorganosiloxanes end-blocked with organosiloxy groups. A third objective is to provide a process where the polyorganosiloxanes have an acceptably low level of residual chloride. A fourth objective is to provide a process where the chlorine displaced from the chlorine-terminated polyorganosiloxane is recovered in a form suitable for use in other processes. A fifth objective of the present invention is to provide a process where chlorine end-terminated polyorganohydrosiloxanes can be processed to form polyorganohydrosiloxanes without significant reaction of the silicon-bonded hydrogen.

SUMMARY OF INVENTION

The present invention is an anhydrous process for preparing organosiloxy end-blocked polyorganosiloxanes from chlorine end-terminated polyorganosiloxanes. The process comprises contacting an anhydrous mixture comprising a chlorine end-terminated polyorganosiloxane and an organodisiloxane with a rearrangement catalyst, where the rearrangement catalyst facilitates a chlorine and organosiloxy exchange between the chlorine end-terminated polyorganosiloxane and the organodisiloxane forming a organochlorosilane as a by-product. The organochlorosilane is continuously removed from the process providing a means by which the chlorine displaced from the chlorine end-terminated polyorganosiloxane can be effectively removed from the organosiloxy end-blocked polyorganosiloxanes in a useable form. The present process is especially useful for the rearrangement of chlorine end-terminated polyorganosiloxanes having one or more hydrogen atoms bonded to silicon to organosiloxy end-blocked polyorganohydrosiloxanes.

DESCRIPTION OF INVENTION The present invention is an anhydrous process for the preparation of organosiloxy end-blocked polyorganosiloxanes. The process comprises:

(A) contacting an anhydrous mixture comprising a chlorine end-terminated polyorganosiloxanes described by formula

$$Cl(R_2SiO)_xSiR_2Cl; \text{ and} \quad (1)$$

an organodisiloxane described by formula

$$R_3SiOSiR_3; \quad (2)$$

with a rearrangement catalyst effective in facilitating a chlorine and organosiloxy exchange between the chlorine end-terminated polyorganosiloxane and the organodisiloxane where organochlorosilane is formed by the exchange;

(B) continuously removing the organochlorosilane from the process: and (C) recovering organosiloxy end-blocked polyorganosiloxanes described by formula

$$R_3SiO(R_2SiO)_ySiR_3; \quad (3)$$

where each R is independently selected from a group consisting of hydrogen atom, alkyls comprising one to 20 carbon atoms, cycloalkyls comprising four to 20 carbon atoms, alkenyls comprising two to 20 carbon atoms, and aryls; $x = 1$ to 1000; and $y = 1$ to 1,001.

The present process can be conducted as a batch, semi-batch, or continuous process. Contact of the anhydrous mixture of the present process with the rearrangement catalyst can be effect in standard type reactors for conducting such reactions. The reactor may be, for example, a stirred-tank reactor, a fixed-bed reactor, or a fluidized-bed reactor.

The present process is conducted as an anhydrous process. By anhydrous, it is meant that the present process does not require the presence of water. For purpose of the present process, an anhydrous mixture is one containing ten weight percent or less of water. Preferred is an anhydrous mixture containing one weight percent or less of water.

The anhydrous mixture useful in the present process comprises a chlorine end-terminated polyorganosiloxane and a organodisiloxane. Chlorine end-terminated polyorganosiloxanes useful in the present invention are described by formula (1). The chlorine end-terminated polyorganosiloxane has substituents R, where each R is independently selected from a group consisting of hydrogen atom, alkyls comprising one to 20 carbon atoms, cycloalkyls comprising four to 20 carbon atoms, alkenyls comprising two to 20 carbon atoms, and aryls. The substituent R can be, for example, methyl, ethyl, propyl, tert-butyl, isobutyl, cyclopentyl, cyclohexyl, cycloheptyl, vinyl, allyl, hexenyl, pentenyl, phenyl, xylyl, and naphthyl. The chlorine end-terminated polyorganosiloxane can have x number of divalent siloxy units of formula $-R_2SiO-$, where R is as previously described, and $x = 1$ to 1000. Preferred are chlorine end-terminated polyorganosiloxanes where $x = 10$ to 200.

The present process is particularly useful for converting chlorine end-terminated polyorganosiloxanes to organosiloxy end-blocked polyorganosiloxanes where at least one R substituent is a hydrogen atom. The reason for this preference is the reactive nature of the hydrogen to silicon bond. Unlike standard practices for converting chlorine end-terminated polyorganosiloxanes to polyorganosiloxanes, the present process has minimal effect on the hydrogen to silicon bond. Therefore, organosiloxy end-blocked polyorganohydrosiloxanes in high yield can be prepared by the present process. Even more preferred are those chlorine end-terminated polyorganosiloxanes where the ratio of hydrogen atoms on the silicon atom to organic substituents on the silicon atom is within a range of about 0.001:1 to about 1:1.

In a preferred process, the chlorine end-terminated polyorganosiloxanes are the product of a hydrolysis process where an organodichlorosilane or diorganodichlorosilane is hydrolyzed in a near stoichiometric equivalence of water. By "near stoichiometric equivalence," it is meant about 0.8 to 1.2 mole of water is added to the hydrolysis process for each mole of organodichlorosilane diorganodichlorosilane. The product of the hydrolysis process may be used in the present process as a mixture of cyclic siloxanes and chlorine end-terminated polyorganosiloxanes or the chlorine end-terminated polyorganosiloxanes may be separated from the cyclic siloxanes prior to use.

The anhydrous mixture useful in the present invention also contains an organodisiloxane as described by formula (2). The organodisiloxane contains substituents R, where R is as previously described for the chlorine end-terminated polyorganosiloxane. For the organodisiloxane, it is preferred that R be selected from a group consisting of hydrogen atom and methyl and that no more than one hydrogen atom be bonded to each silicon. The most preferred organodisiloxane is hexamethyldisiloxane.

The amount of organodisiloxane employed in the process will depended upon the initial degree of polymerization of the chlorine end-terminated polyorganosiloxane and the desired degree of polymerization of the organosiloxy end-blocked polyorganosiloxane. Generally, the larger the amount of organodisiloxane employed in the process, the smaller the degree of polymerization of the organosiloxy end-blocked polyorganosiloxane. A useful amount of organodisiloxane is within a range of about 0.001 mole to 10.0 mole per mole of chlorine added to the process as the end-terminal chlorine of the chlorine end-terminated polyorganosiloxane. A preferred amount of organodisiloxane is within a range of about 0.1 to 2.0 moles per mole of chlorine added to the process as the end-terminated polyorganosiloxane.

The anhydrous mixture comprising a chlorine end-terminated polyorganosiloxane and an organodisiloxane is contacted with a rearrangement catalyst. By "rearrangement catalyst" it is meant those catalyst which facilitate the replacement of the end-terminal chlorine of the chlorine end-terminated polyorganosiloxane with an organosiloxy group originating from the organodisiloxane. In addition, the rearrangement catalyst may effect rearrangement of internal siloxane bonds, i.e. silicon to oxygen bonds, of the chlorine end-terminated polyorganosiloxanes and organosiloxy end-blocked polyorganosiloxanes. In a preferred process, the rearrangement catalyst effects rearrangement of siloxane bonds of the chlorine end-terminated polyorganosiloxanes and of the organosiloxy end-blocked polyorganosiloxanes to form organosiloxy end-blocked polyorganosiloxanes having a higher degree of polymerization than the chlorine end-terminated polyorganosiloxanes added to the process.

The rearrangement catalyst can be either a homogeneous catalyst or a heterogeneous catalyst. Examples of useful homogeneous rearrangement catalysts are: trifluoromethane sulfonic acid, methanesulfonic acid, and trifluoroacetic acid.

Preferred is when the rearrangement catalyst is a heterogeneous catalyst. Even more preferred is when the rearrangement catalyst is a heterogeneous catalyst selected from a group consisting of acid clays, sulfonic acid resins, and activated carbon. The heterogeneous rearrangement catalyst can be in the form of, for example, particles, powders, flakes, chips, or pellets. Any activated carbon capable of facilitating the replacement of the end-terminal chlorine of the chlorine end-terminated polyorganosiloxane with an organosiloxy group originating from the organodisiloxane can be employed in the present process. The activated carbon useful in the present process can be of the thermal or chemically activated type.

Any acid clay capable of facilitating the replacement of the end-terminal chlorine of the chlorine end-terminated polyorganosiloxane with an organosiloxy group originating from the organodisiloxane can be employed in the present process. The acid clays can be, for example, those produced from halloysites, kaolinites, and bentonites composed of montmorillonite; where the clay is treated with an acid solution, for example, sulfuric acid.

Any sulfonic acid resin capable of facilitating the replacement of the end-terminal chlorine of the chlorine end-terminated polyorganosiloxane with an organosiloxy group originating from the organodisiloxane can be employed in the present process. The sulfonic acid resin can be, for example, a synthetic resin having —SO$_3$H or —SO$_2$OH groups attached thereto. The sulfonic acid resin can be for example. Amberlyst A15 (Rhom and Haas, Philadelphia, Pa.) or Dowex DR2040 (The Dow Chemical Company, Midland, Mich.).

The amount of rearrangement catalyst employed in the present process can be varied within wide limits in relation to the chlorine end-terminated polyorganosiloxane added to the process. The amount of rearrangement catalyst will depend upon such factors as the type of catalyst, the specific chlorine end-terminated polyorganosiloxane and organodisiloxane to be rearranged, the process temperature, and whether the process is run as a batch, semi-batch, or continuous process. Examples of useful amount of catalyst are given in the Examples provided herein.

Rearrangement of the chlorine end-terminated polyorganosiloxane with the organodisiloxane results in the organodisiloxane being split into (1) an organosiloxy group which is exchanged for a chlorine of the chlorine end-terminated polyorganosiloxane and (2) a silyl group which serves as a receptor for chlorine to form a chlorosilane which is volatile under process conditions.

The chlorosilane is continuously removed from the process as it is being formed. The chlorosilane can be removed from the process by standard means for separating a gas from a liquid or liquid and solid mixture. The chlorosilane may by removed from the process, for example, by means of a vacuum to draw the chlorosilane into an appropriate storage container or into a process where the chlorosilane serves as a feed.

Polyorganosiloxanes as described by formula (3) are recovered from the process. By the term "recovered" it is meant that the polyorganosiloxanes are appropriately isolated, contained, and stored for their intended use. Preferred polyorganosiloxanes are those in which each substituent R is methyl. Even more preferred are those polyorganosiloxanes in which each substituent R is selected from a group consisting of hydrogen and methyl and no more than one hydrogen is bonded to each silicon atom.

The following examples are provided to illustrate the present process. These examples are not intended to limit the scope of the claims provided herein.

EXAMPLE 1

About 200 g of chlorine end-terminated polymethylhydrosiloxane was added to a flask containing 10 g of a sulfonic acid resin (Amberlyst A-15 Rhom and Haas, Philadelphia, Pa.). Nitrogen was bubbled through the flask contents at a slow rate to remove trimethylchlorosilane formed during the process. About 50 mL of hexamethyldisiloxane was added to the flask over a period of three hours. The content of the flask was kept at a temperature of about 25° C. The nitrogen was allowed to continue to bubble through the flask contents for an additional 16 hours. The flask contents was analyzed by nuclear magnetic resonance and found to comprise 17.8 mole % Me$_3$SiO$_{\frac{1}{2}}$, 82.0 mole % MeHSiO$_{2/2}$, and 0.15 mole % MeSiO$_{3/2}$. Acid content of the flask contents was determined by titration and equated to 99 ppm HCl.

EXAMPLE 2

A 3.6 m by 2.5 cm I.D. teflon reactor was packed with about 227 g of activated carbon (Type: WSIV, Calgon, Philadelphia, Pa.). A mixture comprising 500 g of chlorine end-terminated polymethylhydrosiloxanes and 38 g of hexamethyldisiloxane was fed to the reactor at a rate of 2.1 g/min. The reactor was maintained at a temperature of about 45° C. and a pressure of about 300 mmHg. During conduct of the process a wet nitrogen purge was fed to the reactor counter to the flow of the siloxanes to facilitate removal of trimethylchlorosilane from the process as it was formed. The wet nitrogen purge was created by passing dry nitrogen gas through a 25° C. water bath at a rate of 20 mL/min. prior to the passing of the nitrogen gas into the reactor. A sample of the reactor product was analyzed at the times given in Table 1 for acid content by titration. The results are presented in Table 1 as ppm HCl.

TABLE 1

| Chlorine Content of Polyorganohydrosiloxane | |
|---|---|
| Sampling Time (h) | ppm HCl |
| 2.25 | 20 |
| 2.75 | 12 |
| 4.00 | 11 |

The product was determined to have an Mn of 4590 relative to polystyrene by gel-permeation chromatography.

EXAMPLE 3

The process described in Example 2 was repeated using a mixture of 500 g of chlorine end-terminated polyorganohydrosiloxane and 76.3 g of hexamethyldisiloxane to the reactor. All other process conditions were the same as given for Example 1. A sample of the reactor product was analyzed at the times given in Table 2 for acid content by titration. The results are presented in Table 2 as ppm HCl.

TABLE 2

| Chlorine Content of Polyorganohydrosiloxane | |
|---|---|
| Sampling Time (h) | ppm HCl |
| 0.8 | 2.1 |
| 1.8 | 1.7 |
| 2.8 | 1.7 |

The product was determined to have an Mn of 3134 relative to polystyrene by gel-permeation chromatography.

We claim:

1. A process for preparation of polyorganosiloxanes, the process comprising:
(A) contacting an anhydrous mixture comprising a chlorine end-terminated polyorganosiloxanes described by formula Cl(R$_2$SiO)$_x$SiR$_2$Cl : and an organodisiloxane described by formula R$_3$SiOSiR$_3$;

with a rearrangement catalyst effective in facilitating a chlorine and organosiloxy exchange between the chlorine end-terminated polyorganosiloxane and the organodisiloxane where organochlorosilane is formed by the exchange reaction;
(B) continuously removing the organochlorosilane from the process; and
(C) recovering polyorganosiloxanes described by formula R$_3$SiO(R$_2$SiO)$_y$SiR$_3$;

where each R is independently selected from a group consisting of hydrogen atom, alkyls comprising one to 20 carbon atoms, cycloalkyls comprising four to 20 carbon atoms, alkenyls comprising two to 20 carbon atoms, and aryls; x=1 to 1000: and y=1 to 1,001.

2. A process according to claim 1, where the anhydrous mixture contains one weight percent or less of water.

3. A process according to claim 1, where x=10 to 200.

4. A process according to claim 1, were the chlorine end-terminated polyorganosiloxanes have a ratio of hydrogen atoms on the silicon atoms to organic substituents on the silicon atoms within a range of about 0.001 to about 1:1.

5. A process according to claim 1, where the chlorine end-terminated polyorganosiloxanes are a product of a hydrolysis process where an organodichlorosilane or diorganodichlorosilane is hydrolyzed in a near stoichiometric equivalence of water.

6. A process according to claim 1, where the organodisiloxane is hexamethyldisiloxane.

7. A process according to claim 1, where concentration of organodisiloxane in the anhydrous mixture is within a range of about 0.001 to 10.0 mole per mole of chlorine added to the process as the end-terminal chlorine of the chlorine end-terminated polyorganosiloxanes.

8. A process according to claim 1, where concentration of organodisiloxane in the anhydrous mixture is within a range of about 0.1 to 2.0 mole per mole of chlorine added to the process as the end-terminal chlorine of the chlorine end-terminated polyorganosiloxanes.

9. A process according to claim 1, where the rearrangement catalyst is a homogeneous catalyst.

10. A process according to claim 9, where the rearrangement catalyst is selected from a group consisting of trifluoromethane sulfonic acid, methanesulfonic acid, and trifluoroacetic acid.

11. A process according to claim 1, where the rearrangement catalyst is a heterogeneous catalyst.

12. A process according to claim 11, where the rearrangement catalyst is selected from a group consisting of acid clays, sulfonic acid resins, and activated carbons.

13. A process according to claim 1, where the rearrangement catalyst is an acid clay.

14. A process according to claim 1, where the rearrangement catalyst is a sulfonic acid resin.

15. A process according to claim 14, where the rearrangement catalyst is selected from a group consisting of Amberlyst A15 and Dowex DR2040.

16. A process according to claim 1, where the rearrangement catalyst is an activated carbon.

17. A process according to claim 1, where each substituent R is methyl.

18. A process according to claim 1, where each substituent R is selected from a group consisting of hydrogen and methyl and no more than one hydrogen is bonded to each silicon atom.

19. A process according to claim 1, where the rearrangement catalyst is activated carbon, the anhydrous mixture contains one weight percent or less of water, the organodisiloxane is hexamethyldisiloxane, concentration of the hexamethyldisiloxane in the anhydrous mixture is within a range of about 0.1 to 2.0 mole per mole of chlorine added to the process as the end-terminal chlorine of the chlorine end-terminated polyorganosiloxane, each substituent R is independently selected from a group consisting of hydrogen and methyl and no more than one hydrogen is bonded to each silicon, and x=10 to 200.

20. A process according to claim 19, where the chlorine end-terminated polyorganosiloxanes are a product of a hydrolysis process where an organodichlorosilane or diorganodichlorosilane is hydrolyzed in a near stoichiometric equivalence of water.

21. A process according to claim 1, where the rearrangement catalyst is Amberlyst A15, the anhydrous mixture contains one weight percent or less of water, the organodisiloxane is hexamethyldisiloxane, concentration of the hexamethyldisiloxane in the anhydrous mixture is within a range of about 0.1 to 2.0 mole per mole of chlorine added to the process as the end-terminal chlorine of the chlorine end-terminated polyorganosiloxane, each substituent R is independently selected from a group consisting of hydrogen and methyl and no more than one hydrogen is bonded to each silicon, and x=10 to 200.

22. A process according to claim 21, where the chlorine end-terminated polyorganosiloxanes are a product of a hydrolysis process where an organodichlorosilane or diorganodichlorosilane is hydrolyzed in a near stoichiometric equivalence of water.

* * * * *